United States Patent

Mast, Jr.

[11] 4,053,242
[45] Oct. 11, 1977

[54] DISPOSABLE PRODUCT APPLICATOR AND DISPENSING PACKAGE THEREFOR

[75] Inventor: John George Mast, Jr., Cincinnati, Ohio

[73] Assignee: The Procter & Gamble Company, Cincinnati, Ohio

[21] Appl. No.: 668,253

[22] Filed: Mar. 18, 1976

[51] Int. Cl.² .............................................. A46B 5/02
[52] U.S. Cl. .................................. 401/6; 15/104.94; 15/244 R; 221/232
[58] Field of Search ................ 401/6, 8, 123, 126, 401/130; 15/104.94, 209 R, 209 D, 210, 244 R; 221/232

[56] References Cited

U.S. PATENT DOCUMENTS

| 2,761,166 | 9/1956 | Connolly | 15/210 R X |
| 2,964,772 | 12/1960 | Crawford | 15/244 R |
| 3,299,464 | 1/1967 | O'Brien et al. | 401/130 X |
| 3,362,776 | 1/1968 | Knorr | 401/8 |
| 3,570,036 | 3/1971 | Gilchrist et al. | 15/118 X |

FOREIGN PATENT DOCUMENTS 649,140 12/1928 France ............................... 401/130

Primary Examiner—Robert B. Reeves
Assistant Examiner—Joseph J. Rolla
Attorney, Agent, or Firm—Melville, Strasser, Foster & Hoffman

[57] ABSTRACT

A hand-held, generally T-shaped disposable product applicator and a dispensing package therefor. The applicator comprises a resilient applicator pad portion and an upstanding finger grip portion. The applicator pad portion is normally substantially planar with a top surface and a bottom product applying surface coated or impregnated with the product to be dispensed. The upstanding finger grip portion is normally substantially planar with its sides providing finger grip surfaces. The finger grip portion is substantially normal to and extends transversely across the top surface of the applicator pad portion, bisecting the applicator pad portion into two substantially equal flaps. The applicator pad portion is foldable along its juncture with the finger grip portion with its bottom product applying surface folded upon itself. The finger grip portion is of such thickness that when the applicator pad portion is in its folded condition each half of the applicator pad portion top surface is substantially coplanar with the adjacent finger grip portion side. The dispensing package is adapted to receive a stack of applicators each with its applicator pad portion in folded condition. The package has a dispensing opening through which the handle portion of the end-most applicator of the stack is exposed for removal.

13 Claims, 9 Drawing Figures

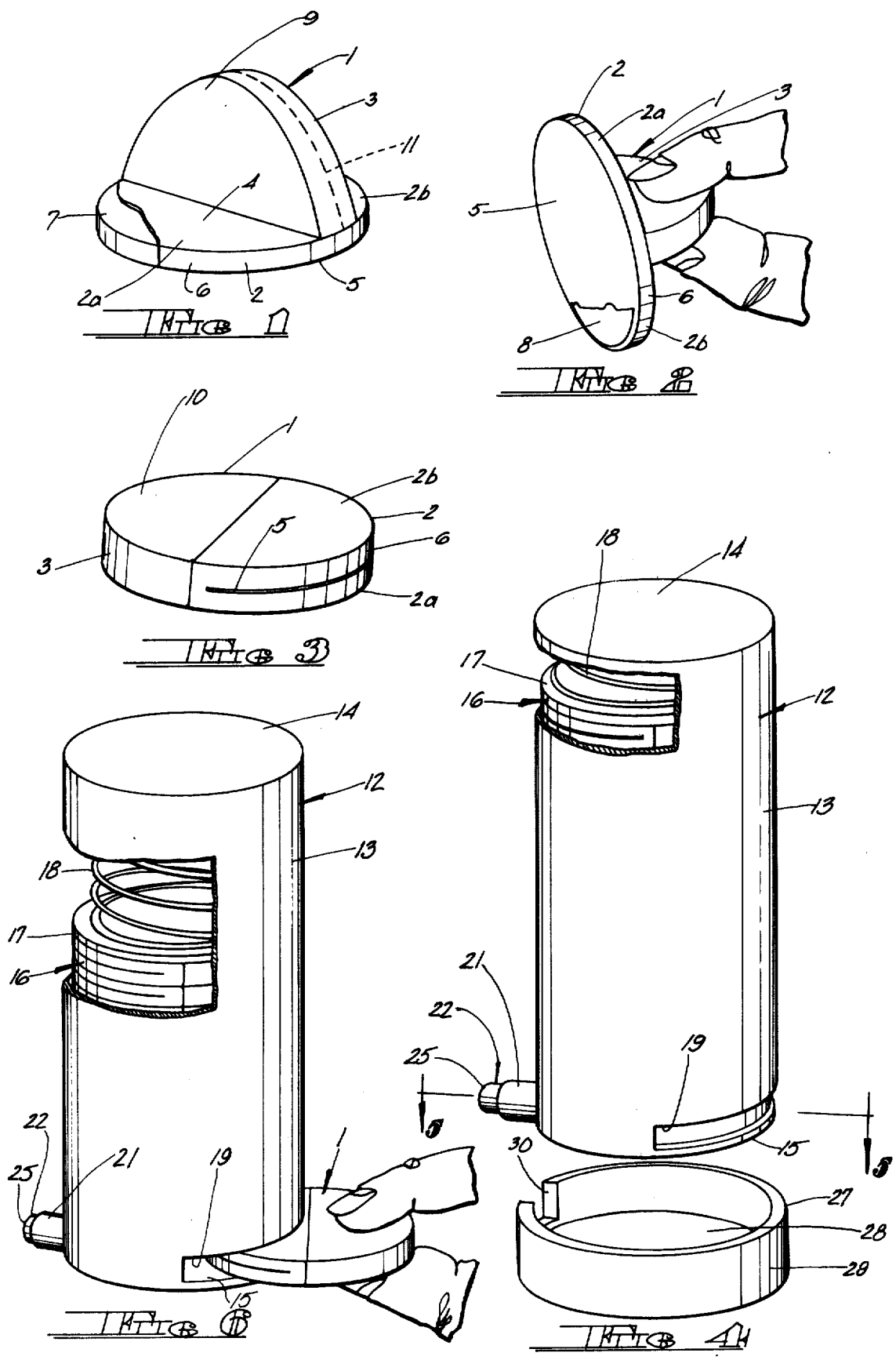

DISPOSABLE PRODUCT APPLICATOR AND DISPENSING PACKAGE THEREFOR

BACKGROUND OF THE INVENTION

1. Field of the Invention

This invention relates to a disposable product applicator and a dispensing package therefor, and more particularly to a hand-held, generally T-shaped disposable product applicator preloaded with a measured quantity of product and a package adapted to contain a stack of the applicators in folded condition and to dispense them one at a time.

2. Description of the Prior Art

Prior art workers have developed various types of resilient applicators, both resuable and disposable in nature. Such applicators have been used to apply to a surface commodities in the form of creams, pastes, gels, liquids, powders and the like. For example, such applicators have been used to apply topical preparations to the skin such as cosmetic products, medicaments and the like. Prior art applicators have been used with a separate product supply or have been impregnated or coated with a measured quantity of product.

By way of example, Graves U.S. Pat. No. 2,932,841 dated Apr. 19, 1960 discloses a substantially rectangular pad of paper or the like furnished with a spot of semi-plastic shoe polish, the pad being folded with the spot of shoe polish on the inside. Connolly U.S. Pat. No. 2,761,166 dated Sept. 4, 1956 discloses a pad of sponge rubber material which is slit inwardly of an edge portion to define a pair of flaps, with dentrifice contained between the flaps. Hume U.S. Pat. No. 2,719,996 dated Oct. 11, 1955 discloses a powder puff comprising a sheet of resilient foam material impregnated with facial powder. The sheet of foam material is folded upon itself with a lip blotter element therebetween and providing a handle projecting through the sheet of foam material.

Applicators having a generally T-shaped configuration are, per se, known in the art. By way of example, Crawford U.S. Pat. No. 2,964,772 dated Dec. 20, 1960 discloses an applicator comprising a resilient disc with a small upstanding handle element. Pad-like applicators with handle portions foldable to an upright position are taught in Anderson et al. U.S. Pat. No. 3,131,410 dated May 5, 1964 and Gilchrist U.S. Pat. No. Re. 26,385 dated May 7, 1968. Perkovich U.S. Pat. No. 3,097,387 dated July 16, 1963 and Perkovich et al. U.S. Pat. No. 3,104,915 dated Sept. 24, 1963 teach generally T-shaped scouring pads.

Prior art workers have devised various dispensing packages for stacked articles of the type wherein the articles are biased toward one end of the package and means are provided for sequentially ejecting the articles from the package or permitting sequential manual removal of the articles therefrom. By way of example, Beardsley U.S. Pat. No. 944,583 dated Dec. 6, 1910 discloses a spring loaded package for a stack of pills or tablets having a sliding end cap for sequentially ejecting tablets contained therein. Gervias U.S. Pat. No. 3,344,951 dated Oct. 3, 1967 discloses a spring loaded package for a stack of pills or tablets wherein a feeding finger sequentially ejects the pills or tablets outwardly through a fenistration in the side of the package. Stewart U.S. Pat. No. 3,393,831 dated July 23, 1968 discloses a dispenser for a stack of razor blades wherein the razor blades are sequentially ejected by means of a sliding follower extending through a slot in the packaged side wall. Seghezzi U.S. Pat. No. 3,588,007 dated Jan. 26, 1971 discloses a dispensing package for a stack of tablet-like articles having a pair of cut out portions adjacent the ends of the stack so that the operator's fingers may be utilized to sequentially slide the tablets from the stack. Danow U.S. Pat. No. 3,578,207 dated May 11, 1971 discloses a dispenser for a stack of bread slices wherein the top-most slice of bread in the stack is surrounded on three sides by a pusher member which, in turn, engages a spring loaded door in the packaged side wall so that the top-most slice may be ejected without being pushed against the spring loaded door. Finally, Hinterreiter U.S. Pat. No. 3,565,284 dated Feb. 23, 1971 teaches a pocket container for tablets or the like having a lever-like ejector for the top-most tablet pivotally affixed to the container cap.

The present invention provides a hand-held, T-shaped disposable product applicator far simpler in construction than those known hitherto. As consequence, they can be more easily and economically produced. The pad portion of the applicator of the present invention is capable of being folded upon itself and in folded condition the applicator is flat and of substantially uniform thickness so that it may readily be stacked in a dispensing container. When removed from the container, the pad portion of each applicator will automatically unfold and assume a product-applying configuration. When the applicator pad portion is in its folded condition, the product applying surface of the applicator is folded upon itself and the product coated on or impregnated in the applying surface of the applicator will be protected from contamination. The users hands are also protected from contact with the applicator surface.

The container of the present invention is adapted to receive a stack of the applicators in folded condition and enables a number of applicators to be compactly stored and readily dispensed. Each applicator is dispensed with its finger grip portion foremost.

SUMMARY OF THE INVENTION

The hand-held, generally T-shaped disposable product applicator of the present invention comprises a resilient applicator pad portion and an upstanding finger grip portion. The applicator pad portion is normally substantially planar and has a bottom product-applying surface coated or impregnated with the product to be dispensed. The pad portion has a top surface from which the finger grip portion (normally substantially planar) extends upwardly. The finger grip portion extends transversely across the upper surface of the pad portion and bisects the pad portion into two substantially equal flaps.

The pad portion of the applicator is foldable along its juncture with the finger grip portion with the product applying surface being folded upon itself. When in its folded condition, the pad portion of the applicator is of substantially the same thickness as the finger grip portion so that the applicator achieves a substantially flat, stackable configuration.

The package of the present invention is adapted to receive a stack of applicators. The package is closed at one end and is provided at or near the other end with an opening from which the applicators may be withdrawn one at a time. Means are provided within the package to advance the stack of applicators as each applicator is removed from the container and to maintain the applicators within the stack in folded condition. The package may be provided with mechanical means to assist in the one-at-a-time dispensing of the applicators and may be provided with an over cap to close the dispensing opening when an applicator is not being dispensed.

BRIEF DESCRIPTION OF THE DRAWINGS

FIG. 1 is a perspective view of the applicator of the present invention.

FIG. 2 is a fragmentary perspective view illustrating the applicator of FIG. 1 in position for use.

FIG. 3 is a perspective view illustrating the applicator of FIG. 1 with its pad portion in folded condition.

FIG. 4 is an exploded view, partly in cross section illustrating the package of the present invention and an over cap therefor.

FIG. 5 is a cross sectional view taken along section line 6—6 of FIG. 4.

DESCRIPTION OF THE PREFERRED EMBODIMENTS

Figure 6:
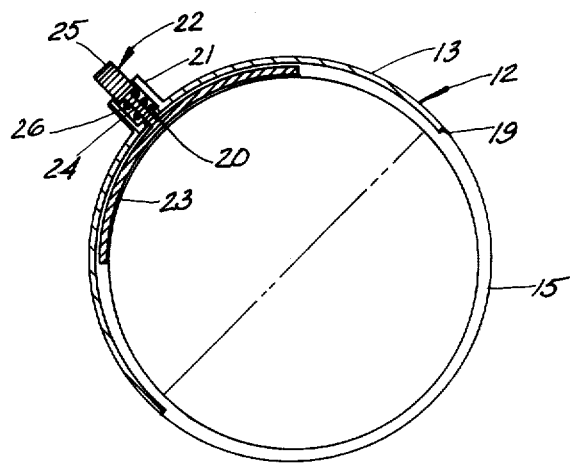
FIG. 6 is a perspective view, partly in cross section, similar to FIG. 4 and illustrating the dispensing of an applicator from the package.

The pad of the present invention is illustrated in FIGS. 1 through 3 wherein like parts have been given like index numerals. The applicator is generally indicated at 1 and comprises a pad portion 2 and a finger grip portion 3. The pad portion 2 is generally planar and may have any appropriate peripheral configuration. For purposes of an exemplary showing, the pad portion 2 is illustrated as being generally disc-shaped with a circular peripheral configuration. Pad portion 2 has a top surface 4 and a bottom product-applying surface 5 (most clearly shown in FIG. 2).

Pad portion 2 and finger grip portion 3 may be of integral, one-piece molded construction, or they may be separately fabricated and joined together, as by means of an appropriate adhesive or the like.

Pad portion 2 is fabricated of a flexible, resilient polymeric foam material non-reactive with the product to be dispensed by the applicator. Exemplary resilient materials include urethane foam, polyethylene foam and the like. While not required, when the finger grip portion 3 is a separate element affixed to the upper surface 4 of pad portion 2, it is preferrably fabricated of the same material.

The product to be dispensed may take any appropriate form including a liquid, a cream, a gel, a paste, a powder or the like. The product is applied to the surface 5 of pad portion 2 and, depending upon the nature of the product, may be coated onto surface 5 or impregnated into pad portion 2. To this end, pad portion 2 may be of open pore foam material such that the product may be impregnated therein, or it may be of closed foam material so as to prevent penetration and migration of the product therethrough. Alternatively, pad portion 2 (and finger grip portion 3, if desired) may be provided with barrier layer (fragmentarily illustrated at 7 in FIG. 1) on either or both of its top surface 4 and side edge 6. The barrier layer may take any appropriate form including an integrally formed skin or a barrier coating, a plastic film or the like laminated or otherwise affixed to pad portion 2 to prevent migration of the product outwardly of the pad portion through its edge 6 or top surface 4.

It is also within the scope of the invention to provide product-applying surface 5 of pad portion 2 with means for increasing its texture, as is fragmentarily shown at 8 in FIG. 2. These means may include abrasive means, flocking, a layer of woven or knitted cloth, netting or the like. The texture-increasing means enables the product to be more forcefully applied, as by scrubbing action. Further, product-applying surface 5 of pad portions 2 may be of a controlled pore structure to control the rate of deposition of a liquid product, for example, impregnated into the pores of the applicator pad.

As pointed out above, the finger grip portion 3 may be an integral, one-piece part of pad portion 2. For purposes of an exemplary illustration, finger grip portion 3 is illustrated as being a separate element affixed to the upper surface 4 of pad portion 2. The peripheral configuration of finger grip portion 3 does not constitute a limitation on the present invention. For purposes of an exemplary showing it is illustrated as being substantially semi-circular and of a diameter substantially equal to the diameter of disc-like pad portion 2.

Finger grip portion 3 provides two finger grip surfaces 9 and 10 (see FIGS. 1 and 3). An exemplary manner of engagement of surfaces 9 and 10 by the fingers of the user is shown in FIG. 2. Finger grip portion 3 is substantially normal to pad portion 2 and extends diametrically thereacross, preferably bisecting pad portion 2 into two equal halves or flaps 2a and 2b. It is preferable that finger grip portion 3 substantially bisect pad portion 2 irrespective of the peripheral configuration of pad portion 2.

As pointed out heretofor, pad portion 2 is resilient and normally assumes and remains in the substantially planar configuration illustrated in FIGS. 1 and 2 when unconstrained. Nevertheless, the halves 2a and 2b of pad portion 2 may be folded upon each other as illustrated in FIG. 3. Under these circumstances, applying surface 5 is folded upon itself and is located between pad portion halves 2a and 2b. In the folded configuration illustrated in FIG. 3 the pad portion halves are substantially coplanar with surfaces 9 and 10 of the finger grip portion 3 so that the applicator 1 assumes a flat, substantially planar, disc-like configuration of substantially uniform thickness. This will render a series of applicators, when in folded condition, readily stackable.

To achieve the uniform thickness of the folded applicator, finger grip portion 3 is of a thickness approximately twice that of pad portion 2 when in unfolded condition. When pad portion 2 and finger grip portion 3 are separate pieces joined together, finger grip portion 3 may simply be made of a thickness twice that of pad portion 2 or finger grip portion 3 may be made of two plys appropriately joined together by adhesive or the like, each ply being of substantially the same thickness as pad portion 2. This is indicated by broken line 11 of FIG. 1.

FIGS. 4 through 6 illustrate the package of the present invention. The package is generally indicated at 12. The package comprises a cylindrical or tubular wall 13 closed at its upper end by a circular top portion 14 and at its bottom end by a circular bottom portion 15. For purposes of an exemplary showing the package 12 is illustrated as being cylindrical with an internal diameter slightly greater than the diameter of the folded disc-like applicator illustrated in FIG. 3. It will be understood by one skilled in the art that if the applicator, when folded, has a peripheral configuration other than circular, container 13 may be provided with an accommodating cross sectional configuration.

Within package 13 there is disposed a stack of applicators in folded condition (as shown in FIG. 3). This stack is generally indicated at 16. Stack 16 is surmounted by a follower 17 and a long stroke spring 18. One end of spring 18 abuts top portion 14 of the container, while the other end of the spring abuts follower 17. The spring and follower assembly urge stack 16 downwardly and maintain the individual applicators of the stack in their folded condition.

Near bottom 15 of package 12 the cylindrical wall 13 is provided with a slot 19 of a width at least equal to the thickness of an applicator in folded condition as packaged and of a length to extend approximately half way around package wall 12 (see FIG. 6). Preferably, the width of slot 12 is slightly more than the thickness of a folded applicator as packaged but less than twice the thickness thereof.

Package 12 may be provided with hand-actuated means by which the lowermost applicator of stack 16 may be pushed partially outwardly through slot 19 so that the pad may be grasped by the user's fingers. Reference is made to FIG. 5 wherein like parts have been given like index numerals. Opposite slot 19, cylindrical wall 13 of container 12 is provided with a perforation 20. The perforation 20 is surrounded by a cylindrical boss 21 extending laterally from package wall 13 and having an internal diameter slightly greater than perforation 20. A pusher element generally indicated at 22 comprises an arcuate portion 23 located within container 12 and being of such diameter as to normally lie adjacent the inside surface of package wall 13. Arcuate portion 23 has a shaft portion 24 extending through perforation 20 and into boss 21. The free end of shaft 24 is provided with a push button portion 25 of a diameter substantially equal to the internal diameter of boss 21. A compression spring 26 is captively mounted on shaft 24. One end of spring 26 abuts package wall 13 within boss 21, while its other end abuts push button 25. It will be understood from FIG. 5 that spring 26 will tend to urge the pusher assembly to the retracted position illustrated in FIG. 5.

Referring to FIGS. 5 and 6 (like parts having been given like index numerals in FIG. 6), it will be understood that the individual applicators of stack 16 will be so oriented that as each applicator is dispensed through slot 19, its finger grip portion 3 will be presented foremost to the user. To remove an applicator from the package, it is only necessary to depress push button 25 against the action of spring 26. This will result in the partial advancement of the finger grip portion of the lowermost applicator (generally indicated at 1) of stack 16 through slot 19. As is shown in FIG. 6, the finger grip portion of applicator 1 may then be grasped by the user and the applicator may be removed from package 12. Upon removal from package 12, the pad portion of applicator 1 will spring to its normal planar position as illustrated in FIG. 2.

Release of push button 25 will cause the pusher assembly to return to the position illustrated in FIG. 5. The follower 17 spring 18 assembly will advance stack 16 downwardly until the next lowermost applicator of the stack abuts package bottom 15. The package is then ready to have the dispensing operation performed again.

It will be undertood by one skilled in the art that the package of FIGS. 4 through 6 may be provided with an overcap to close slot 19 when the package is not in use. This might help to enable the package to maintain the stack of applicators fresh and free from contamination. Such an overcap is illustrated at 27 in FIG. 4.

The precise nature and configuration of overcap 27 does not constitute a limitation on the present invention. For purposes of an exemplary showing, the overcap is illustrated as having a circular bottom 28 and a peripheral upstanding flange 29. Peripheral flange 29 may be so sized as to frictionally engage the bottom portion of package 12. Other means well known in the art may be used to maintain overcap 27 in position on the bottom portion of package 12. Upstanding flange 29 is shown having a notch 30 so sized as to accommodate the package boss 21.

Figure 7:
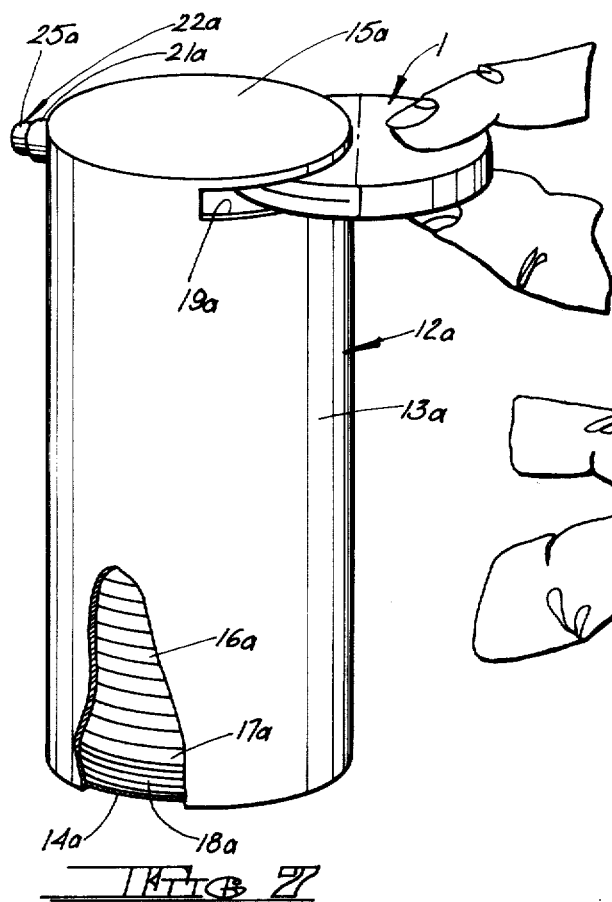
FIG. 7 is a perspective view of another embodiment of the package of the present invention.

FIG. 7 illustrates another embodiment of the package of the present invention. The package of FIG. 7 differs from that of FIGS. 4 through 6 only in that the slot and pusher assembly are located at the upper end of the package while the spring and follower assembly within the package are located at the bottom thereof. With this reversal top-for-bottom of the parts kept in mind, like parts have been given like index numerals followed by "a". With the exception that stack 16a will be advanced upwardly by follower 17a and spring 18a, the operation of the package of FIG. 7 will otherwise be identical to that described with respect to the package of FIGS. 4 through 6. Package 12a may be provided with an overcap of any appropriate type, including one identical to overcap 27 of FIG. 4.

Figure 8:
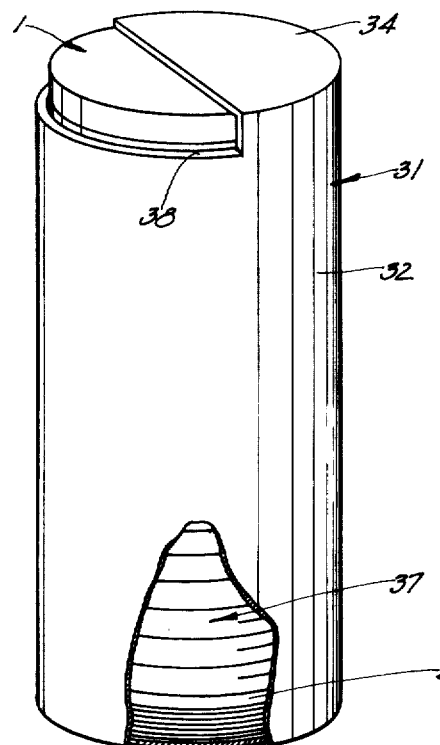
FIG. 8 is a perspective view of yet another embodiment of the package of the present invention.
Figure 9:
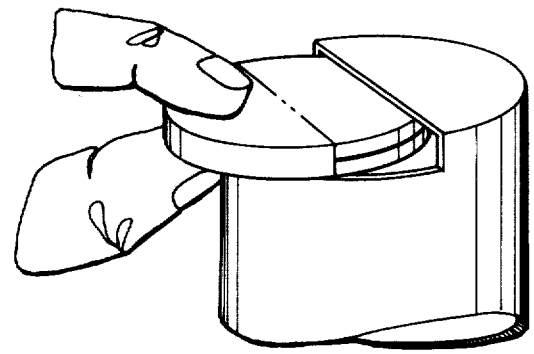
FIG. 9 is a fragmentary view illustrating the dispensing of an applicator from the package of FIG. 8.

FIGS. 8 and 9 illustrate yet another embodiment of the package of the present invention. Again, for purposes of an exemplary showing, the package is illustrated as accommodating a stack of folded applicators of the type illustrated in FIG. 3. To this end the package, generally indicated at 31, has a cylindrical side wall 32 a circular bottom 33 and a substantially semi-circular top 34. It will be understood by one skilled in the art that a package incorporating the same principles as that of FIGS. 8 and 9 could be made to accommodate applicators having, when folded, a different peripheral configuration than the applicator of FIG. 3.

Package 31 contains a follower 35 and a long stroke spring 36 between follower 35 and bottom 33. A stack of applicators is generally indicated at 37.

The package of FIGS. 8 and 9 is intended to enable sequential removal of the applicators therefrom by hand and without the aid of a mechanical pusher or other device. This is accomplished by the provision of the semi-circular top 34 and a cooperating notch 38 in package side 32 whereby the finger grip portion of the topmost applicator (generally indicated at 1) is sufficiently exposed to permit the finger grip portion to be engaged by the user and the top-most applicator to be removed from package 31, as is illustrated in FIG. 9 wherein like parts have been given like index numerals.

As in the case of slot 19 of the package of FIG. 4, notch 38 should be of such depth as to permit convenient removal of the top most applicator 1. Preferably, notch 38 is of a depth slightly greater than the thickness of an applicator with its pad portion folded and less than twice the thickness thereof.

It will be understood that each applicator of stack 37 will be so oriented as to present its finger grip portion to the user. As applicators are removed from package 31, the follower 35spring 36 assembly will advance the stack 37 upwardly. Package 31 may be provided with an overcap of any appropriate type. The overcap may, for example, be similar to that illustrated in FIG. 4 with the exception that no notch (equivalent to notch 30 of FIG. 4) is required. It will further be understood that the package of FIGS. 8 and 9 may be inverted end-for-end (in much the same manner described with respect to the packages of FIGS. 4 and 7) so that applicators may be dispensed from the bottom thereof.

All of the packages described above may be fabricated of any suitable material including metal, plastic, paper board or the like. If desired, all of the packages may be refillable and reusable. All of the packages may be provided with bracket means (not shown) for mounting on a appropriate surface such as a wall surface or the like.

Modifications may be made in the invention without departing from the spirit of it. For example, for increased product protection and particularly in an embodiment of the applicator wherein the finger grip portion 3 is made up of two plies (see FIG. 1), the product may be located in the finger grip portion 3 and forced to the pad portion 2 at the time of use by squeezing finger grip portion surfaces 9 and 10. In such an embodiment, it would be desirable to provide means to assure that the product migrates to pad portion 2 rather than through the finger grip portion. For example, the surfaces 9 and 10 and the edges of finger grip portion 3 could have a barrier thereon of any of the types described above with respect to FIG. 1. On the other hand, the finger grip portion 3 could be formed of a closed pore material or the product could be located within its own rupturable container.

The applicators of the present invention may be packaged individually or in packages other than those described above. If provided with an envelop-type package, for example, the package may be so sized as to maintain the applicator in the folded condition illustrated in FIG. 3. Where the type of package used is not such that it will maintain the applicator in folded position, flaps 2a and 2b of pad portion 2 may be maintained in folded position by any type of appropriate sealing means such as tape, hot melt, glue or the like.

In a package of the type described with respect to FIGS. 4 through 6 or in an inverted version of the package of FIGS. 8 and 9, the spring-follower assemblies may be eliminated and a weight substituted therefor to advance the stack and to maintain the applicators in folded condition. A spring loaded pivot, a deformable panel or other mechanical means may be substituted for the pusher assembly of FIGS. 4 through 7.

While the applicators have been, for purposes of an exemplary showing, described as being made of foam, it will be understood by one skilled in the art that other materials could be used so long as they are compatable with the product to be dispensed.

The embodiments of the invention in which an exclusive property or privilege is claimed are defined as follows:

1. A hand-held, T-shaped disposable product applicator comprising a resilient, integral, one-piece structure having an applicator pad portion and an upstanding finger grip portion, said pad portion being normally substantially planar with a top surface and a bottom product-applying surface, said upstanding finger grip portion being normally substantially planar with opposite sides providing finger grip surfaces, said finger grip portion being normally substantially normal to and extending transversely across said top surface of said pad portion bisecting said pad portion into two substantially equal parts, said pad portion being foldable along its juncture with said finger grip portion with said bottom product applying surface folded upon itself, said finger grip portion being of a thickness substantially twice the thickness of said pad portion whereby when said applicator pad portion is folded, said finger grip portion and said folded pad portion are substantially coplanar and of substantially the same thickness.

2. The structure claimed in claim 1 wherein said pad portion is disc-shaped with a circular peripheral configuration, said finger grip portion being of semi-circular configuration with a diameter equal to the diameter of said pad portion, said finger grip portion extending diametrically of said top surface of said pad portion whereby when said pad portion is in said folded condition said applicator is substantially flat, disc-like and of substantially uniform thickness.

3. The structure claimed in claim 1 wherein said pad portion comprises a controlled pore structure.

4. The structure claimed in claim 1 including a textured layer on said product-applying bottom surface of said pad portion.

5. The structure claimed in claim 1 wherein at least said applicator pad portion is fabricated of a flexible resilient, polymeric foam material non-reactive with product to be dispensed by said applicator.

6. The structure claimed in claim 5 wherein said finger grip portion is fabricated of said flexible, resilient, polymeric foam material.

7. The structure claimed in claim 1 wherein a product to be applied by said applicator is coated on said bottom product-applying surface of said pad portion.

8. The structure claimed in claim 7 wherein said pad portion at least of said applicator is fabricated of a flexible resilient closed foam material.

9. The structure claimed in claim 1 wherein a product to be applied by said applicator is impregnated in said pad portion.

10. The structure claimed in claim 9 wherein said pad portion at least of said applicator is fabricated of a flexible, resilient open foam material.

11. The structure claimed in claim 9 wherein said pad portion of said applicator has at least one peripheral edge, a barrier layer on at least one of said top surface and said peripheral edge to prevent migration of said product therethrough.

12. The structure claimed in claim 1 wherein said pad portion of said applicator has at least one peripheral edge, a barrier layer on at least one of said top surface and said peripheral edge to prevent migration of said product therethrough.

13. The structure claimed in claim 12 including a barrier layer covering said finger grip portion.

* * * * *